United States Patent
Kirn et al.

(10) Patent No.: US 11,724,036 B2
(45) Date of Patent: Aug. 15, 2023

(54) SYRINGE FOR PROCESSING FAT GRAFTS AND RELATED METHODS

(71) Applicant: Werd, LLC, Lexington, KY (US)

(72) Inventors: David S. Kirn, Lexington, KY (US); Richard D. Hisel, Nicholasville, KY (US); William Whitman, Nicholasville, KY (US)

(73) Assignee: Orchid Holdings, LLC, Lexington, KY (US)

( * ) Notice: Subject to any disclaimer, the term of this patent is extended or adjusted under 35 U.S.C. 154(b) by 847 days.

(21) Appl. No.: 16/466,411

(22) PCT Filed: Nov. 29, 2017

(86) PCT No.: PCT/US2017/063678
§ 371 (c)(1),
(2) Date: Jun. 4, 2019

(87) PCT Pub. No.: WO2018/111550
PCT Pub. Date: Jun. 21, 2018

(65) Prior Publication Data
US 2019/0328977 A1 Oct. 31, 2019

Related U.S. Application Data

(60) Provisional application No. 62/432,882, filed on Dec. 12, 2016.

(51) Int. Cl.
*A61M 5/31* (2006.01)
*A61M 5/178* (2006.01)
(Continued)

(52) U.S. Cl.
CPC ............ *A61M 5/3145* (2013.01); *A61M 1/76* (2021.05); *A61M 1/88* (2021.05); *A61M 5/1782* (2013.01);
(Continued)

(58) Field of Classification Search
CPC ........ A61M 1/88; A61M 5/3145; A61M 1/64; A61M 1/67; A61M 5/3134; A61M 5/3135; A61M 5/178–3129
See application file for complete search history.

(56) References Cited

U.S. PATENT DOCUMENTS 4,128,692 A 12/1978 Reid
5,338,294 A * 8/1994 Blake, III ............. A61M 1/772
604/38

(Continued)

*Primary Examiner* — Erich G Herbermann
*Assistant Examiner* — Linnae E. Raymond
(74) *Attorney, Agent, or Firm* — Michael S. Hargis; Stites & Harbison PLLC (57) ABSTRACT

A syringe for withdrawing an aspirate from a body for micro fat grafting is provided. The syringe includes a barrel having an inner wall extending therein. The inner wall has one or more apertures formed therein allowing the aspirate to contact an absorbent positioned between the inner wall and an outer wall of the barrel. A plunger moves longitudinally within the barrel along the inner wall and has a gasket attached to a proximal end forming a seal against the inner wall. The absorbent may take many forms to absorb a non-fat cell portion of the aspirate. A related method includes retracting the plunger from a first position to draw the aspirate from a harvest site of a body into the barrel, exposing the aspirate to the absorbent, and moving the plunger toward the first position so a remaining portion of the aspirate is no longer exposed to the absorbent.

27 Claims, 8 Drawing Sheets

(51) Int. Cl.
*A61M 5/315* (2006.01)
*A61M 1/00* (2006.01)
*A61B 17/00* (2006.01)

(52) U.S. Cl.
CPC .............. *A61M 5/31531* (2013.01); *A61B 2017/00792* (2013.01); *A61M 2005/3114* (2013.01); *A61M 2202/08* (2013.01); *A61M 2205/75* (2013.01)

(56) References Cited

U.S. PATENT DOCUMENTS

| | | | |
|---|---|---|---|
| 5,512,054 A * | 4/1996 | Morningstar | A61M 5/31511 604/218 |
| 6,403,857 B1 | 6/2002 | Gross et al. | |
| 9,581,942 B1 * | 2/2017 | Shippert | G03G 15/20 |
| 2006/0093527 A1 * | 5/2006 | Buss | A61M 1/85 435/297.2 |
| 2006/0213374 A1 | 9/2006 | Shipped | |
| 2010/0112696 A1 | 5/2010 | Min | |
| 2012/0175319 A1 | 7/2012 | Cotton et al. | |
| 2012/0191053 A1 | 7/2012 | Hu et al. | |
| 2013/0030322 A1 * | 1/2013 | Levine | A61B 10/0283 600/566 |
| 2013/0158515 A1 * | 6/2013 | Austen, Jr. | A61M 5/14526 604/152 |
| 2014/0171861 A1 | 6/2014 | Stroumpoulis | |
| 2015/0352266 A1 * | 12/2015 | Gourlay | A61M 1/67 604/542 |

* cited by examiner

SYRINGE FOR PROCESSING FAT GRAFTS AND RELATED METHODS

This application is the national stage of international patent application no. PCT/US2017/63678 filed on Nov. 29, 2017, which in turn claims priority from U.S. Provisional Patent Application Ser. No. 62/432,882 filed on Dec. 12, 2016, the disclosures of each of which are incorporated herein by reference in their entirety.

TECHNICAL FIELD

The invention generally relates to a syringe for harvesting, processing, and re-introducing a small volume fat graft into patients.

BACKGROUND

The process of micro fat grafting involves the suction aspiration, e.g. liposuction, of small amounts of fat from a harvest site of a patient, and subsequent re-injection of the fat into a grafting site of the same patient. The aspirate is harvested from an area of the patient in which an excess of fat resides, such as the patient's thighs, abdomen, or hips. The aspirate typically includes fat cells, local anesthetic, oil from ruptured fat cells, and blood. In order to deliver a high-quality fat cell graft, viable fat cells must be gently separated from the other components of the aspirate. Excess or rough processing of the fat cells can damage the viable cells. If the fat cells are damaged, they will not take and will die when re-introduced to the body leading to poor long-term results. Hence, the goal is to re-introduce or graft as many viable fat cells as possible and minimize the re-introduction of the non-viable cells and other components of the aspirate.

The most common micro fat grafting technique involves an initial liposuction of aspirate with a syringe and a harvesting cannula. The surgeon creates a vacuum inside the syringe which draws the aspirate through the cannula and into the barrel of the syringe. Although the aspirate could be directly re-injected into the grafting site, it is preferential to separate the fat cells from the remaining aspirate since only the fat cells are capable of maintaining viability in the grafting site. Therein are currently several methods for separating fat cells from the remaining aspirate for grafting including, processing the aspirate via centrifuge, filtering or washing the aspirate, using a washing vessel, and/or simply waiting for gravity to separate the fat cells from the remaining aspirate.

With most existing methods of fat cell harvesting, the fat cells must be removed from a harvesting container, processed, and transferred into one or more syringes for re-injection. Hence, these methods involve substantial handling of the fat cells and possibly generating trauma thereto. Even more, significant mechanical forces are applied to the fat cells with centrifugation and some of the known filtration methods which can lead to cellular damage. Transferring and processing the fat cells also requires significant time and exposes the fat cells to potential contamination during the open transfer process. Accordingly, a need exists to effectively harvest fat cells, separate the viable fat cells from the oil and fluid of the remaining aspirate in a gentle and timely manner, minimize or eliminate vessel transfer, i.e., utilize a closed system, and re-introduce viable fat cells back into the patient thereby minimizing the number of apoptotic cells in the graft.

SUMMARY OF THE INVENTION

In accordance with the purposes and benefits described herein, a syringe for withdrawing an aspirate from a body for micro fat grafting includes a barrel having an inner wall extending therein, the inner wall having one or more apertures formed therein, an absorbent positioned between the inner wall and an outer wall of the barrel, and a plunger for longitudinal movement within the barrel along the inner wall, the plunger having a gasket attached to a proximal end of the plunger forming a seal.

In another possible embodiment, the inner wall and the outer wall define a chamber along at least a length of the barrel and the absorbent is positioned within the chamber. In still another possible embodiment, the chamber is defined along substantially an entire length of the barrel.

In yet another possible embodiment, the one or more apertures are formed in a first portion of the inner wall. In still yet another possible embodiment, the chamber is defined along the first portion of the inner wall wherein the one or more apertures are formed. In one other possible embodiment, a second portion of the inner wall is impermeable.

In another possible embodiment, the syringe further includes a second plunger concentrically positioned with the plunger. In yet another possible embodiment, the second plunger includes a gasket attached to a proximal end of the second plunger forming a seal against the plunger.

In still another possible embodiment, the syringe further includes a filter extending within the chamber and positioned between the inner wall and the absorbent. In another possible embodiment, the filter is a cotton gauze, a mesh filter, a tine mesh filter, a paper, and/or an absorptive paper.

In still other possible embodiments, the absorbent may be a cotton, a super absorbent-embedded cotton, the absorbent may include fibers, at least a first portion of the fibers may wick and absorb oil, at least a second portion of the fibers may wick and absorb aqueous fluids, the absorbent may include a superabsorbent material, the superabsorbent material may be a superabsorbent polymer, the absorbent may include at least a first layer of fibers and a second layer of a superabsorbent material, and/or the absorbent may include fibers and a superabsorbent material mixed homogeneously, and/or varying combinations of the above.

In one additional possible embodiment, a syringe for withdrawing an aspirate from a body for micro fat grafting includes a barrel having first and second portions, the first portion having an inner wall with a lesser diameter than an inner wall of the second portion, a sleeve having one or more apertures extends within the second portion of the barrel, an absorbent positioned between the sleeve and the second portion inner wall, and a plunger for longitudinal movement within the barrel along the first portion inner wall and the sleeve, the plunger having a gasket attached to a proximal end of the plunger forming a seal.

In another possible embodiment, the sleeve and the second portion inner wall define a chamber along at least a length of the barrel second portion and the absorbent is positioned within the chamber. In still another possible embodiment, the chamber is defined along substantially an entire length of the barrel second portion.

In one other possible embodiment, the syringe further includes a second plunger concentrically positioned with the plunger. In still another possible embodiment, the second plunger includes a gasket attached to a proximal end of the second plunger forming a seal against the plunger.

In another possible embodiment, the syringe includes a second sleeve having one or more apertures, the second sleeve extending within the second portion of the barrel and at least partially defining the chamber.

In still another possible embodiment, the at least one of the sleeve and the second sleeve rotate relative the other such that in a first relative position, the sleeve and the second sleeve form a closed cylinder and in a second relative position, the sleeve and the second sleeve form a cylinder having one or more apertures.

In still yet other possible embodiments, the absorbent is wrapped around the sleeve. In still other possible embodiments, a first layer of fibers is wrapped around the sleeve and a second layer of absorbent is wrapped around the first layer of fibers. In still more possible embodiments, the absorbent is formed into a cylinder and slid over the sleeve.

In accordance with the purposes and benefits described herein, a method is provided of securing fat cells for micro fat grafting using a syringe. The method may be broadly described as comprising the steps of: (a) retracting a plunger from a first position in order to draw an aspirate from a harvest site of a body into a barrel of the syringe; (b) exposing the aspirate to an absorbent for absorbing a portion of the aspirate; and (c) moving the plunger toward the first position such that a remaining portion of the aspirate is no longer exposed to the absorbent.

In another possible embodiment, the moving step includes the step of returning the remaining portion of the aspirate to a grafting site of the body.

In still another possible embodiment, the absorbent is positioned between an inner wall and an outer wall of the barrel.

In yet another possible embodiment, the barrel includes first and second portions, the first portion having an inner wall with a lesser diameter than an inner wall of the second portion, the syringe includes a sleeve having one or more apertures and extending within the second portion inner wall, and the absorbent is positioned between the sleeve and the second portion inner wall.

In still yet another possible embodiment, the plunger is fully inserted in the syringe in the first position and the retracting step moves the plunger from the first position to a second position such that a gasket attached to a proximal end of the plunger is adjacent a distal end of a first portion of the barrel.

In another possible embodiment, the exposing step includes the step of further retracting the plunger from the second position to a third position such that the aspirate is exposed to the absorbent.

In yet another possible embodiment, the moving step includes moving the plunger from the third position to the second position.

In still another possible embodiment, the exposing step includes the step of filtering the aspirate.

In one other possible embodiment, the plunger is fully inserted in the syringe in the first position and the retracting step moves the plunger from the first position to a second position such that the aspirate is exposed to the absorbent. In another possible embodiment, the moving step includes moving the plunger from the second position to the first position.

In yet another possible embodiment, the moving step includes the step of returning the remaining portion of the aspirate to a grafting site of the body.

In other possible embodiments, the method may further include the step of agitating the syringe to promote absorption. In still other possible embodiments, the agitating step may include at least one of the steps of rolling, rotating, and shaking the syringe.

In still other possible embodiments, the exposing step may further include the step of wicking the first portion of the aspirate toward the absorbent.

In yet still other possible embodiments, the method may further include the step of expelling or transferring at least a portion of the remaining portion of the aspirate into one or more syringes.

In one other possible embodiment, the retracting step may include retracting a second plunger positioned within the plunger. In another possible embodiment, the second plunger includes a gasket attached to a proximal end of the second plunger forming a seal against the plunger.

In yet another possible embodiment, the retracting step moves the plunger and the second plunger from the first position to a second position such that the aspirate is exposed to the absorbent.

In one other possible embodiment, the method further includes the step of moving the second plunger toward the first position such that at least a portion of a remaining portion of the aspirate is returned to a grafting site of the body.

In the following description, there are shown and described several preferred embodiments of the syringe for withdrawing an aspirate from a body for micro fat grafting and related methods of securing fat cells for micro fat grafting using a syringe. As it should be realized, the syringes and related methods are capable of other, different embodiments and their several details are capable of modification in various, obvious aspects all without departing from the assemblies as set forth and described in the following claims. Accordingly, the drawings and descriptions should be regarded as illustrative in nature and not as restrictive.

BRIEF DESCRIPTION OF THE DRAWING FIGURES

The accompanying drawing figures incorporated herein and forming a part of the specification, illustrate several aspects of the syringes and methods and together with the description serve to explain certain principles thereof. In the drawing figures.

Reference will now be made in detail to the present embodiments of the syringe and related methods, examples of which are illustrated in the accompanying drawing figures, wherein like numerals are used to represent like elements.

DETAILED DESCRIPTION

Figure 1:
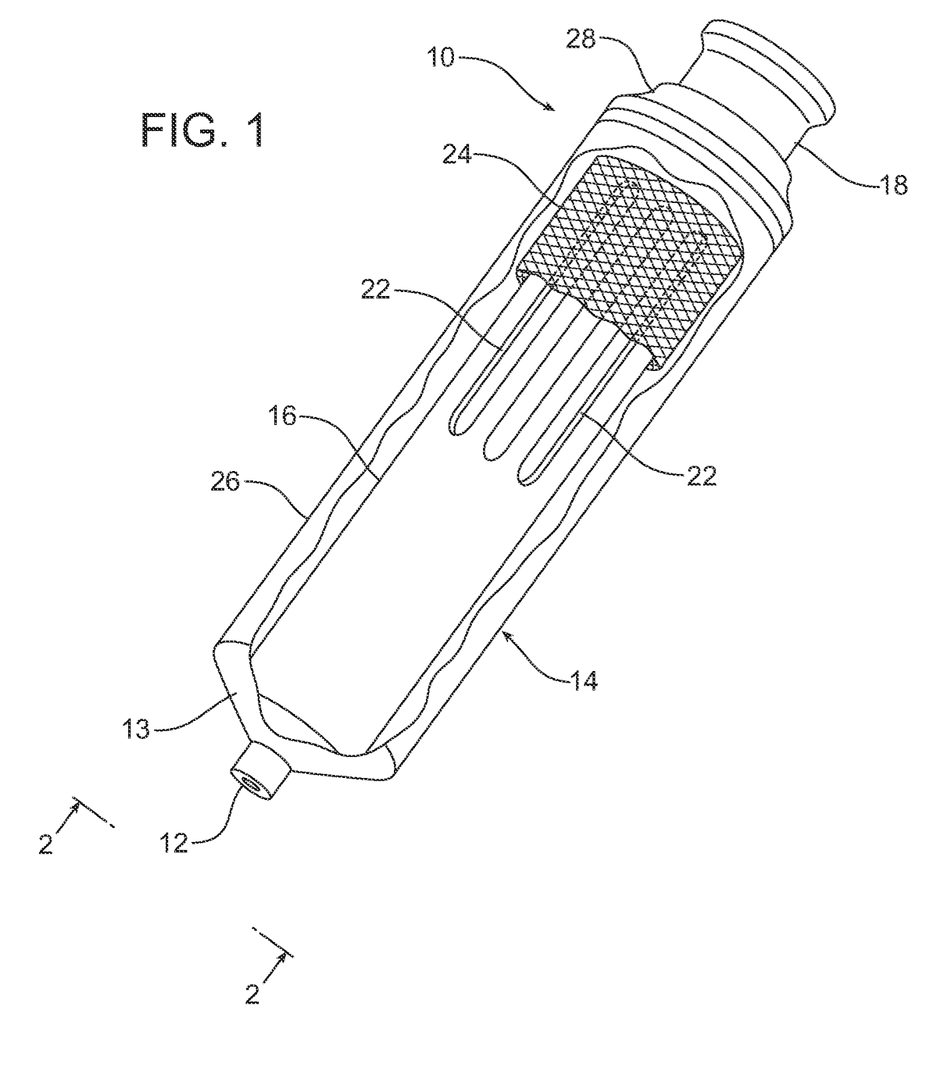
FIG. 1 is a perspective, partial cut-away view of a syringe for withdrawing aspirate from a body for micro fat grafting.

Reference is made to FIG. 1 which illustrates a syringe 10 for withdrawing an aspirate from a harvest site of a human body for micro fat grafting. The syringe 10 includes a fluid fitting 12 located at a proximal end 13 of a barrel 14 consistent with an industry standard medical syringe. In the described embodiment, the fluid fitting 12 is a male Luer-Lok connection fitting designed to mate with a female Luer-Lok fitting. A fat harvesting cannula, hypodermic needle, liposuction cannula, or other extraction device (not shown) is connected to the fluid fitting 12.

The barrel 14 has an inner wall 16 extending therein generally defining a channel. A plunger 18 moves longitudinally within the channel and a gasket 20 attached to a proximal end of the plunger forms a seal against the inner wall 16. As is known in the art, retraction of the plunger 18 within the channel creates a vacuum allowing for the aspirate to be extracted from the body, through the extraction device, and into the channel. In other words, retraction of the plunger 18 from a first position draws the aspirate from the harvest site of the body into a barrel 14 of the syringe 10.

As shown in FIG. 1, one or more apertures 22 are formed in the inner wall 16. In the described embodiment, the one or more apertures 22 include a plurality of slots which are formed in and extend along a first portion of the inner wall 16. A second portion of the inner wall 16 is impermeable. Accordingly, the one or more apertures 22 allow the aspirate to be exposed to the absorbent 24 when the plunger 18 is retracted into the first portion of the syringe 10. The one or more apertures 22 are optimally configured to maximize surface area for contact with an absorbent 24, described in detail below, yet maintain structural integrity of the inner wall 16. As the aspirate contacts the absorbent 24, a portion of the aspirate including aqueous fluids, for example, blood, anesthetic, saline, and oil is wicked out of the aspirate and absorbed into the absorbent. In alternate embodiments, the one or more apertures 22 may include any number, shape and/or size of aperture and/or combinations thereof.

Figure 8:
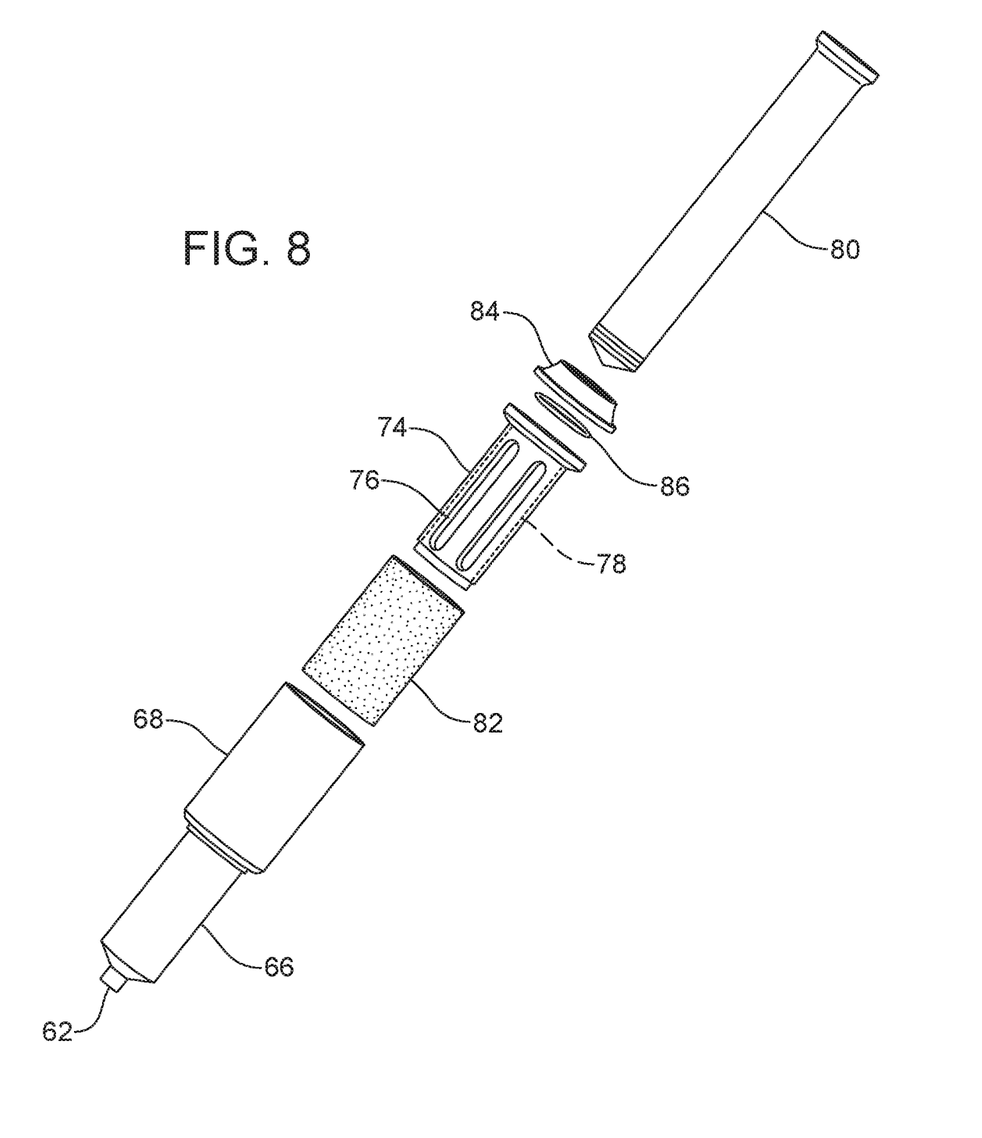
FIG. 8 is an exploded view of the syringe shown in FIG. 7.

In the described embodiment, the inner wall 16 and an outer wall 26 of the barrel 14 generally define a chamber. A cap 28 and a seal (as shown in FIG. 8) are supported at a distal end of the barrel 14 preventing leaking along the plunger 18 and further defining the chamber. The chamber is in fluid communication with the channel along at least a length of the barrel 14 within which the absorbent 24 is positioned. As shown in FIG. 1, the chamber is defined and extends along substantially an entire length of the barrel 14. In alternate embodiments, the chamber may extend along only the first portion of the inner wall 16 corresponding to the one or more apertures 22, as shown in FIG. 1, or along any portion.

Figure 2:
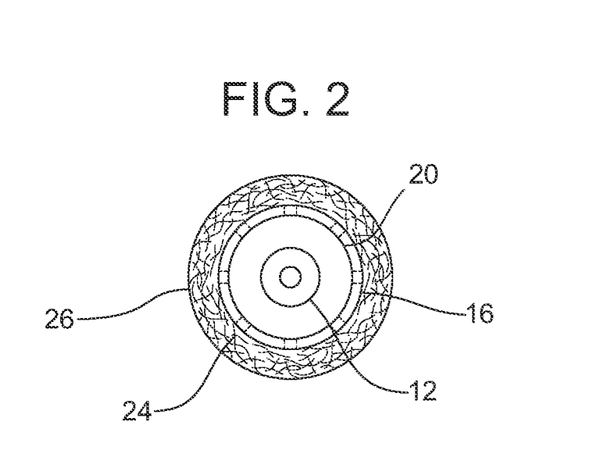
FIG. 2 is a section cut end view of the syringe.

The absorbent 24 may simply be any material capable of retaining fluid. For instance, the absorbent 24 may include a cotton, a super absorbent-embedded cotton, a superabsorbent material, or a superabsorbent polymer. in the described embodiment, however, the absorbent 24 is a multi-component absorbent arranged in a homogenous manner as shown in FIG. 2.

The multi-component absorbent 24 includes fibers which wick and/or absorb oils from ruptured fat cells. Such fibers may include, for example, combed or straightened cotton fibers that can soak up oil by letting it flow into channel-like spaces that form between the fibers relying on capillary action. Further, cotton fibers provide both adsorption wherein the oil merely adheres to the fibers and absorption into the fibers. A second fiber component includes fibers which wick and/or absorb aqueous fluids such as saline, blood, and local anesthetic and a third component includes a material for trapping or locking in the wicked fluids. Such a material may include, for example, a sodium polyacrylate or other superabsorbent material. All three of these components, or combinations of any two or more, may be arranged in such a way as to maximize their effectiveness.

Figure 3:
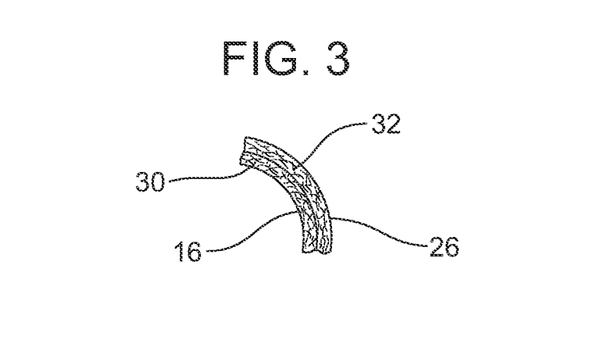
FIG. 3 is a section cut end view of an alternate embodiment of the syringe.

In another embodiment, the previously mentioned absorbent components may be situated in layers arranged and varied in either a vertical, a radial, or an angular pattern with respect to a central axis of the syringe 10. As shown in FIG. 3, a first layer 30 may include the first and second fiber components for wicking oils and aqueous fluids, and a second layer 32 may include the material for locking in the wicked oil and fluid.

Figure 4:
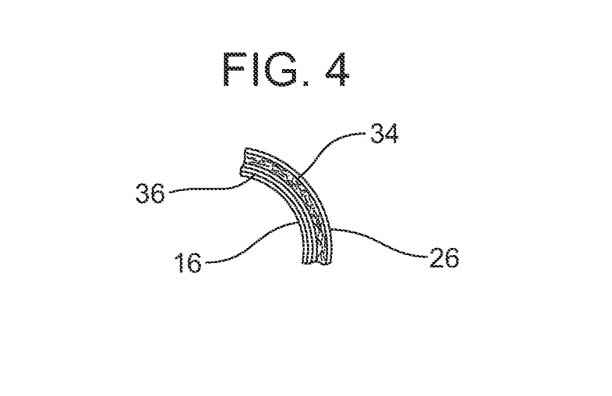
FIG. 4 is a section cut end view of another alternate embodiment of the syringe.

As shown in FIG. 4, the absorbent may be configured as a cartridge 34 in another embodiment and inserted into the chamber as a unit during manufacture or at the time of use. The cartridge 34 may be stamped or otherwise formed and slid into the chamber around the inner wall 16. In this embodiment, a filter 36 is utilized to prevent viable fat cells from passing out of the channel into the chamber. The filter 36 extends within the chamber and is positioned between the inner wall 16 and the absorbent 24. While not limited to these examples, the filter 36 may be a cotton gauze, a mesh filter, a fine mesh filter, a paper, an absorptive paper, a semipermeable membrane, and/or a perforated polymer sheet.

As described above, retraction of the plunger 18 from a first position draws the aspirate from the harvest site of the body into a barrel 14 of the syringe 10. The aspirate is exposed to an absorbent 24 for absorbing a portion of the aspirate leaving another portion of the aspirate including viable fat cells in the channel of the syringe 10. In accordance with a method of securing fat cells for micro fat grafting, the plunger 18 is moved toward the first position such that the remaining portion of the aspirate is no longer exposed to the absorbent 24. In this position, the remaining portion of the aspirate including the viable fat cells is positioned within the barrel 14 of the syringe 10 and may be returned to the grafting site of the body.

As described above, different embodiments of the syringe 10 include varying absorbents and may include a filter 36 to aid in separating the liquid portions of the aspirate from the viable fat cells. In such embodiments, the exposing step may further include wicking the first portion of the aspirate and/or filtering the aspirate. Even more, with the plunger 18 retracted from the first position such that the aspirate is exposed to the absorbent, the syringe 10 may be agitated to promote absorption. Agitating the syringe 10 may include rolling and/or shaking the syringe by mechanical or physical means and/or rotating the syringe along its long axis. More specifically, an external device may be utilized to roll and/or shake the syringe 10 and aspirate therein or the syringe could be placed on a rotating external appliance which would utilize centrifugal force to drive the fluid portion of the aspirate into the absorbent 24.

Once the viable fat cells are separated from the first or liquid portion of the aspirate and positioned within the barrel 14 of the syringe 10 as described above, the viable fat cells or fat graft is ready for re-introduction at the grafting site of the body. The same syringe 10 may be used to re-inject the viable fat cells or, if the user prefers, the fat graft may be transferred or expelled in one or more portions to one or more smaller syringes.

Figure 5:
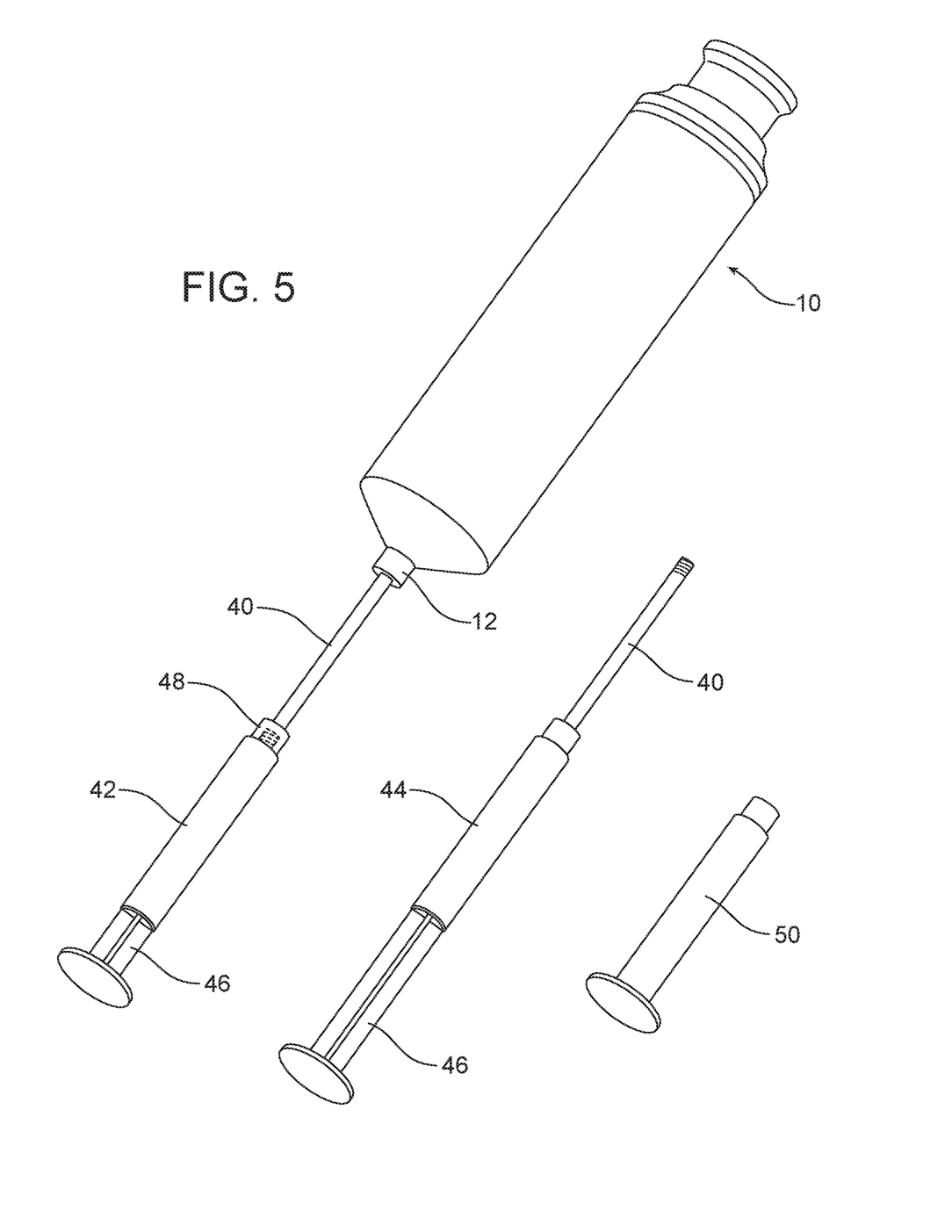
FIG. 5 is an illustration of the syringe transferring a fat graft to a series of smaller syringes.

As shown in FIG. 5, the transfer to the smaller syringes may be accomplished in a closed system utilizing the Luer-Lok connection fitting 12 of the syringe 10. A tube 40 is connected at a first end to the fitting 12 of syringe 10 and at a second end to a first smaller syringe 42. A second smaller syringe 44 is shown with a plunger 46 in a retracted position and a cap 48 securing a portion of the fat graft in the syringe. A third smaller syringe 50 is also shown.

Figure 6:
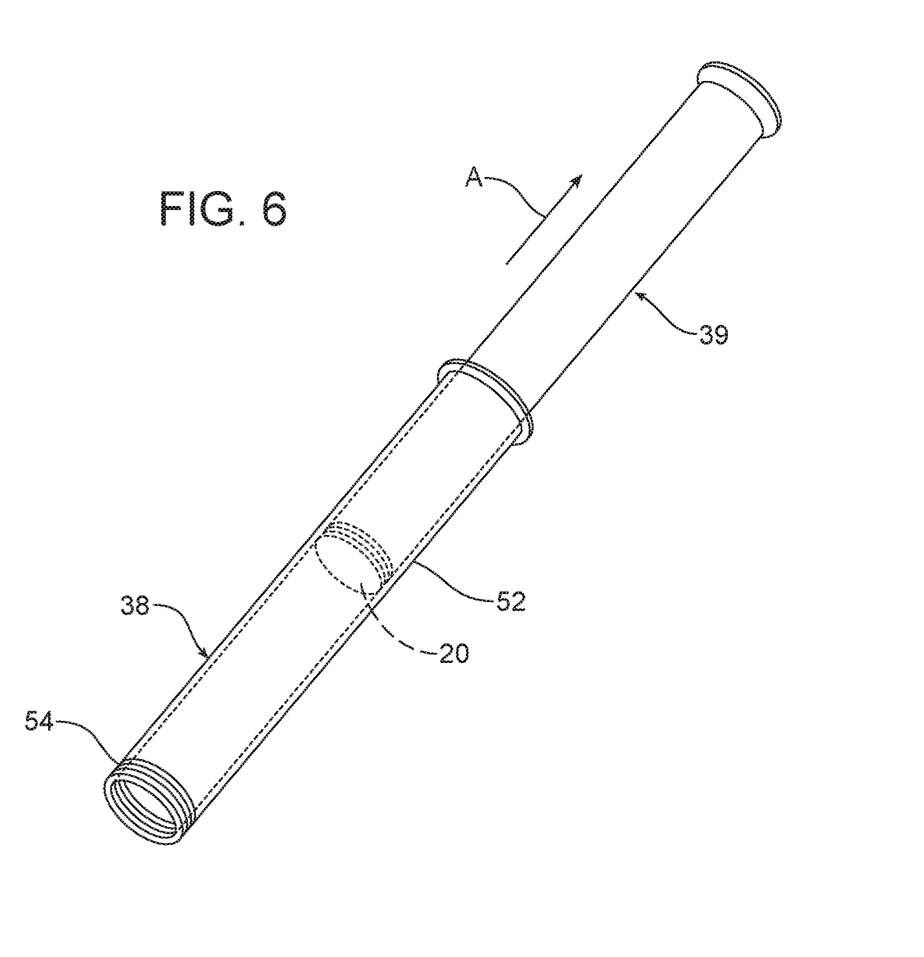
FIG. 6 is a perspective view of a first plunger extending from a second plunger in an alternate embodiment syringe.

In another embodiment shown in FIG. 6, the syringe 10 includes a second plunger 38. As shown, the second plunger 38 is concentrically positioned with a first plunger 39. In this embodiment, the second plunger 38 is an outer plunger having a thin, tubular wall 52 allowing the plunger 39, i.e., the inner plunger, to move inside of the outer plunger 38. An outer gasket or O-ring 54 is positioned at a proximal end of the outer plunger 38 to seal against the inner wall 16 of the syringe barrel 14. The gasket 20 located at the proximal end of the inner plunger 39 seals against an inside of the wall 52 of the outer plunger 38.

In this configuration, when the outer plunger 38 is withdrawn from a first position, the inner plunger 39 is retracted concomitantly, thereby creating a vacuum in the barrel 14. Retracting the inner plunger 39 from the first position to a second position exposes the aspirate to the absorbent 24. If the inner plunger 39 is further retracted (as shown by action arrow A) leaving the outer plunger 38 in the second position, the remaining aspirate in the barrel 14 will move into a chamber generally defined by the tubular wall 52 and gasket 20. During re-injection of the fat graft to a grafting site of the body, the tubular wall 52 of the outer plunger 38 is moved from the second position and utilized to occlude the one or more apertures formed in the inner wall 16 of the barrel 14. This prevents the remaining portion of the aspirate, including the viable fat cells, from being forced into the absorbent 24 as the fat graft is forced from the chamber of the outer plunger 38 through movement of the plunger 39.

Figure 7:
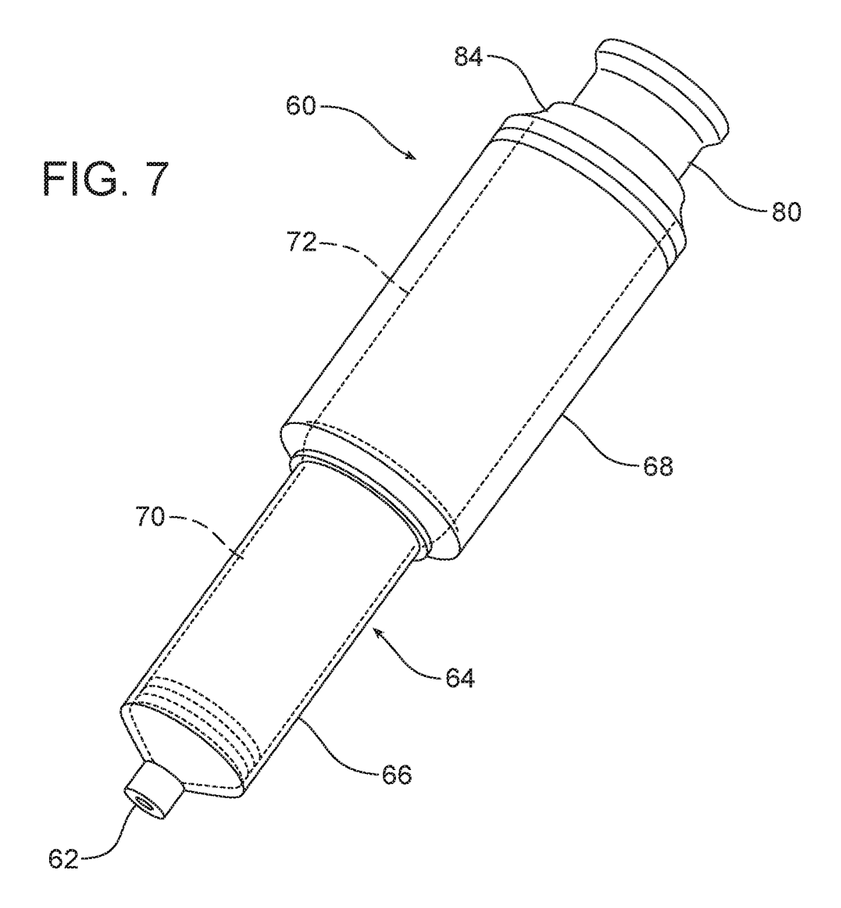
FIG. 7 is a perspective view of another embodiment of a syringe for withdrawing aspirate from a body for micro fat grafting having first and second portions of differing inner diameters.

Reference is now made to FIG. 7 which illustrates an alternate embodiment of a syringe 60 for withdrawing an aspirate from a harvest site of a human body for micro fat grafting. The syringe 60 includes a fluid fitting 62 located at a proximal end of a barrel 64 consistent with an industry standard medical syringe. In the described embodiment, the fluid fitting 62 is a male Luer-Lok connection fitting designed to mate with a female Luer-Lok fitting. A fat harvesting cannula, hypodermic needle, liposuction cannula, or other extraction device (not shown) is connected to the fluid fitting 62.

The barrel 64 includes first and second portions 66, 68. The first portion 66 has an inner wall 70 with a lesser diameter than a diameter of an inner wall 72 of the second portion 68. As best shown in FIG. 8, a sleeve 74 having one or more apertures 76 formed therein extends within the second portion 68 of the barrel 64. More specifically, the inner wall 72 extending within the second portion 68 generally defines a channel within which the sleeve 74 extends. Similarly, an inner wall 78 of the sleeve 74 defines a channel having an inner diameter substantially the same as the inner diameter of a channel generally defined by the inner wall 70 extending within the first portion of the barrel 66.

A plunger 80 moves longitudinally within the channels defined by the inner walls 70 and 78, and a gasket 86 attached to a proximal end of the plunger forms a seal against the inner wall 70. As described above, retraction of the plunger 80 within the channel defined by the inner walls 70 creates a vacuum allowing for the aspirate to be extracted from the body, through the extraction device, and into the syringe 60. In other words, retraction of the plunger 80 from a first position draws the aspirate from the harvest site of the body into the barrel 64 of the syringe 60. In this embodiment, the plunger 80 is fully inserted in the syringe 60 in the first position and is retracted to a second position such that the gasket 86 attached to the proximal end of the plunger is adjacent a distal end of the first portion of the barrel 66.

In the described embodiment shown in FIG. 8, the one or more apertures 76 include a plurality of slots formed in and extending along the sleeve 74. Accordingly, the one or more apertures 76 allow the aspirate to be exposed to an absorbent 82 when the plunger 80 is further retracted from the second position to a third position. As described above, the one or more apertures 76 are optimally configured to maximize surface area for contact with the absorbent 82 yet maintain structural integrity of the inner wall 78. As the aspirate contacts the absorbent 82, a portion of the aspirate including aqueous fluids is wicked out of the aspirate and absorbed into the absorbent. In alternate embodiments, the one or more apertures 76 may include any number, shape and/or size of aperture and/or combinations thereof.

In this described embodiment, the inner wall 72 of the barrel 64 and the sleeve 74 generally define a chamber. A cap 84 and a seal 86 are supported at a distal end of the barrel 64 preventing leaking along the plunger 80 and further defining the chamber. The chamber is in fluid communication with the channel formed by the inner wall 78 of the sleeve 74, and the absorbent 82 is positioned within the chamber. As shown, the chamber is defined and extends along substantially an entire length of the second portion 68 of the barrel 64. In alternate embodiments, the chamber may extend along any portion of the second portion 68 of the barrel 64.

As described in detail above, the absorbent 82 may simply be any material capable of retaining fluid. In this described embodiment, however, the absorbent 82 is a multi-component absorbent arranged in a homogenous manner as a cartridge as shown in FIG. 8. The cartridge is inserted into the chamber as a unit during manufacture or at the time of use. In another embodiment, as described above, a filter may be utilized to prevent viable fat cells from passing out of the channel into the chamber. Such a filter would extend within the chamber and be positioned between the sleeve 74 and the absorbent 82 in a manner similar to the filter 36 shown in FIG. 3 extends between wall 16 and absorbent 34.

As described above, retraction of the plunger 80 from the first position draws the aspirate from the harvest site of the body into the barrel 64 of the syringe 60. Further retracting the plunger 80 from the second position to a third position exposes the aspirate to the absorbent 82. The absorbent absorbs a portion of the aspirate leaving another portion of the aspirate, including viable fat cells, in the channel of the syringe 60. In accordance with the method of securing fat cells for micro fat grafting, the plunger 80 is moved from the third position toward the first position such that the remaining portion of the aspirate is no longer exposed to the absorbent 82. In this position, the remaining portion of the aspirate including the viable fat cells is positioned within the first portion 66 of the barrel 64 of the syringe 60 and may be returned to the grafting site of the body.

As described above, different embodiments of the syringe 60 include varying absorbents and may include a filter to aid in separating the liquid portions of the aspirate from the viable fat cells. In such embodiments, the exposing step may further include wicking the first portion of the aspirate and/or filtering the aspirate. Even more, with the plunger 80 retracted from the first position such that the aspirate is exposed to the absorbent, the syringe 60 may be agitated to promote absorption. Agitating the syringe 60 may include rolling, rotating, and/or shaking the syringe by mechanical or physical means.

Once the viable fat cells are separated from the first or liquid portion of the aspirate and positioned within the first portion 66 of the barrel 64 of the syringe 60 as described above, the viable fat cells or fat graft is ready for re-introduction at the grafting site of the body by moving the plunger 80 from the second position toward the first position. The same syringe 60 may be used to re-inject the viable fat cells or, if the user prefers, the fat graft may be transferred or expelled in one or more portions to one or more smaller syringes in a closed system as generally shown in FIG. 5. In other words, the tube 40 connects to the syringe 60 and the fat graft transfers to the smaller syringes 42, 44, and 50 in the same manner as described.

Figure 9:
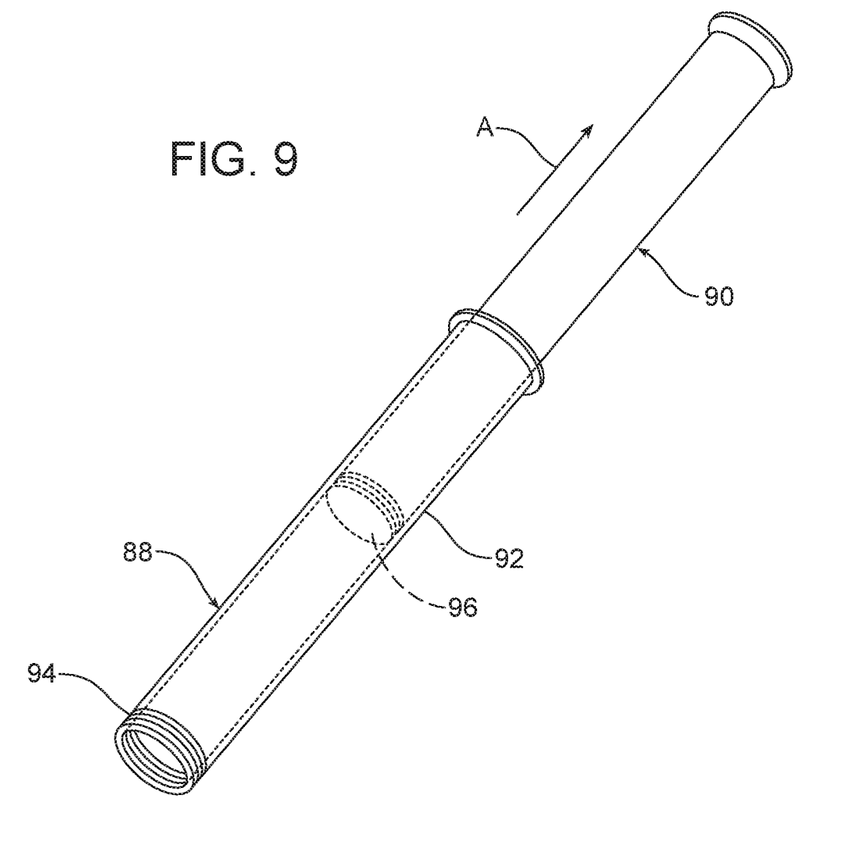
FIG. 9 is a perspective view of a first plunger extending from a second plunger in yet another embodiment of a syringe having first and second portions of differing inner diameters.

In still another embodiment, the syringe 60 includes a second plunger 88. As shown, the second plunger 88 is concentrically positioned with a first plunger 90. In this embodiment, the second plunger 88 is an outer plunger having a thin, tubular wall 92 allowing the plunger 80, i.e., the inner plunger, to move inside of the outer plunger 88. An outer gasket or O-ring 94 is positioned at a proximal end of the outer plunger 88 to seal against the inner wall 70 of the first portion 66 of the barrel 64. A gasket 96 located at the proximal end of the inner plunger 90 seals against an inside of the wall of the outer plunger 88.

In this configuration, when the outer plunger 88 is withdrawn from a first position, the inner plunger 90 is retracted concomitantly, thereby creating a vacuum in the first portion 66 of the barrel 64. Retracting the inner and outer plungers 90, 88 from the first position to a second position exposes the aspirate to the absorbent 82. If the inner plunger 90 is further retracted leaving the outer plunger 88 in the second position, the remaining aspirate in the barrel 64 is drawn into a chamber generally defined by an inner wall 92 of the outer plunger 88 and gasket 96. During re-injection of the fat graft to a grafting site of the body, the tubular wall 92 of the outer plunger 88 is moved from the third position to at least the second position and utilized to occlude the one or more apertures 76 formed in the sleeve 74. This prevents the remaining portion of the aspirate, including the viable fat cells, from being forced into the absorbent 82 as the fat graft is forced from the chamber of the outer plunger 88 through movement of the plunger 90.

In using the syringe embodiments described, a puncture incision is made by the user in the desired harvest site of the human body. A harvesting device, such as a cannula, is connected to a syringe by means of a Luer lock fitting, or other fitting, located at the proximal aspect of the syringe barrel. The cannula is inserted into the body; the user withdraws a plunger of the syringe and moves the cannula in a manner familiar to those skilled in the art. A vacuum pressure created in a barrel of the syringe results in aspirate being drawn into the barrel. As the procedure continues, the user further withdraws the plunger to maintain a consistent, low vacuum. Graduations printed on the syringe barrel reveal an amount of aspirate collected. In one embodiment, a releasable plunger holding mechanism locks the plunger at whatever position it is withdrawn to, thereby avoiding the need for the user to hold the plunger in the desired position. This process continues until a desired quantity of aspirate has been obtained or at least a proximal aspect of the barrel is full.

The cannula is subsequently removed from the body and the syringe is oriented with a proximal tip pointing up. The surgeon then retracts the plunger fully until it contacts a stop created by a top cap in the described embodiment. in this way, the entire contents of the aspirate are exposed to an absorbent via the apertures. Once the plunger is retracted, the syringe can either be left in the vertical position, or lightly agitated in either a rolling, rotating, and/or shaking manner. After a period allowing for fluid absorption, with the syringe held upright, the user returns the plunger thereby pushing the fat cells to the proximal aspect of the barrel and expelling any remaining air. The same cannula used for harvesting, a different one, a hypodermic needle, or other re-insertion device is then re-attached to the fitting. The re-insertion device is inserted into the body at the graft site. The plunger is then pushed forward expelling the processed fat graft through the cannula and into the graft site. In an alternate embodiment, the processed graft may be pushed out into another container, or syringe(s), in an open or a closed transfer process. The described syringes are intended for discard after a single use.

Figure 10:
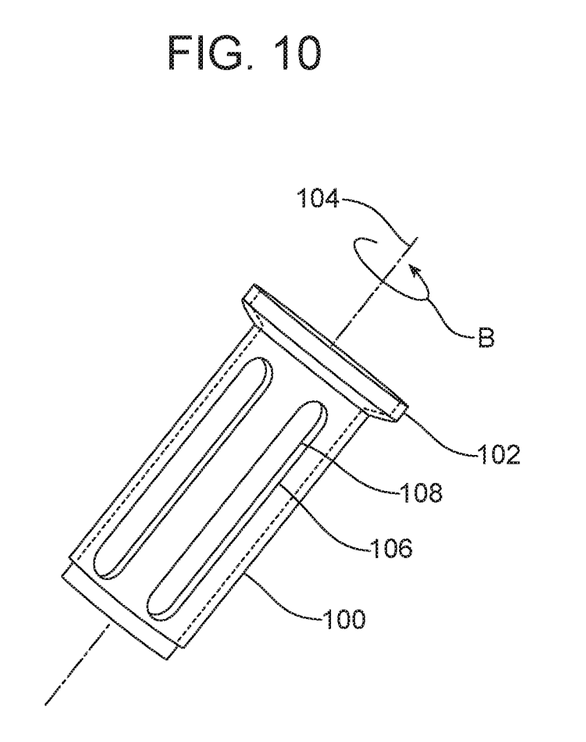
FIG. 10 is a perspective view of first and second nested sleeves that may be used in an alternate embodiment of a syringe.

In summary, numerous benefits result from a syringe for withdrawing an aspirate from a body for micro fat grafting and related methods of securing fat cells for micro fat grafting using a syringe. The foregoing has been presented for purposes of illustration and description. It is not intended to be exhaustive or to limit the embodiments to the precise form disclosed. Obvious modifications and variations are possible in light of the above teachings. For example, first and second nested sleeves 100, 102 may rotate relative one another about an axis 104 as shown by action arrow B in FIG. 10. The nested sleeves 100, 102 could replace sleeve 74, for example, in the above-described syringe 60. In rotating sleeves 100, 102 in this manner, respective apertures 106, 108 may align relative one another allowing an aspirate within a syringe barrel to be in communication with an absorbent. Further rotation can close the one or more apertures preventing the aspirate from contacting the absorbent.

In addition, a plunger locking mechanism may be utilized with any of the described embodiments including, for example, a releasable holding system that locks the plunger in a partially withdrawn position when retracted, a friction lock mechanism, a flexible rubber flange that wedges against the plunger cylinder, an offset collar that wedges against the plunger cylinder, or a ratchet system which indexes against the plunger cylinder at specified points. Each of these locking mechanisms are generally known in the industry and each serves to maintain a vacuum in at least a proximal portion of the syringe barrel. All such modifications and variations are within the scope of the appended claims when interpreted in accordance with the breadth to which they are fairly, legally and equitably entitled.

What is claimed:
1. A syringe for withdrawing an aspirate from a body, comprising:
   a barrel including first and second portions, the first portion having a lesser diameter than the second portion;

a single sleeve extending within the second portion, the single sleeve having one or more apertures formed therein;

an absorbent positioned within the second portion;

a plunger for longitudinal movement within the first and second portions of the barrel; and a gasket attached to an end of the plunger forming a seal via contact with an inner wall of the first portion of the barrel and the sleeve, wherein the one or more single sleeve apertures provide continuous fluid communication between the absorbent and a channel at least partially defined by the sleeve when the plunger is retracted to position at least a portion of the aspirate in the second portion of the barrel.

2. The syringe for withdrawing an aspirate from a body of claim 1, wherein a diameter of the first portion inner wall is substantially the same as a diameter of an inner wall of the sleeve.

3. The syringe for withdrawing an aspirate from a body of claim 2, further comprising a second plunger concentrically positioned with the plunger.

4. The syringe for withdrawing an aspirate from a body of claim 1, wherein the barrel second portion and the sleeve define a chamber and the absorbent is positioned within the chamber.

5. The syringe for withdrawing an aspirate from a body of claim 4, wherein the chamber is further defined by a cap and a seal.

6. The syringe for withdrawing an aspirate from a body of claim 4, further comprising a filter extending within the chamber and positioned between the sleeve and the absorbent.

7. The syringe for withdrawing an aspirate from a body of claim 6, wherein the filter is selected from the group consisting of a cotton gauze, a mesh filter, a fine mesh filter, a paper, or an absorptive paper.

8. The syringe for withdrawing an aspirate from a body of claim 1, wherein the absorbent is a cotton.

9. The syringe for withdrawing an aspirate from a body of claim 1, wherein the absorbent is a super absorbent-embedded cotton.

10. The syringe for withdrawing an aspirate from a body of claim 1, wherein the absorbent includes fibers.

11. The syringe for withdrawing an aspirate from a body of claim 10, wherein at least a first portion of the fibers wick and absorb oil.

12. The syringe for withdrawing an aspirate from a body of claim 11, wherein at least a second portion of the fibers wick and absorb aqueous fluids.

13. The syringe for withdrawing an aspirate from a body of claim 1, wherein the absorbent includes a superabsorbent material.

14. The syringe for withdrawing an aspirate from a body of claim 13, wherein the superabsorbent material is a superabsorbent polymer.

15. The syringe for withdrawing an aspirate from a body of claim 1, wherein the absorbent includes at least a first layer of fibers and a second layer of a superabsorbent material.

16. The syringe for withdrawing an aspirate from a body of claim 1, wherein the absorbent includes fibers and a superabsorbent material homogeneously combined.

17. A method of securing fat cells for micro fat grafting using the syringe of claim 1, comprising the steps of:

retracting the plunger from a first position in order to draw the aspirate from a harvest site of the body into the barrel of the syringe;

exposing the aspirate to the absorbent for absorbing a portion of the aspirate; and moving the plunger toward the first position such that a remaining portion of the aspirate is no longer exposed to the absorbent.

18. The method of securing fat cells for micro fat grafting using a syringe of claim 17, wherein the plunger is fully inserted in the syringe in the first position and the retracting step moves the plunger from the first position to a second position such that the gasket attached to a proximal end of the plunger is adjacent to a distal end of the barrel.

19. The method of securing fat cells for micro fat grafting using a syringe of claim 18, wherein the exposing step includes the step of further retracting the plunger from the second position to a third position.

20. The method of securing fat cells for micro fat grafting using a syringe of claim 19, wherein the moving step includes moving the plunger from the third position to the second position.

21. The method of securing fat cells for micro fat grafting using a syringe of claim 17, wherein the exposing step includes the step of filtering the aspirate.

22. The method of securing fat cells for micro fat grafting using a syringe of claim 17, wherein the moving step includes the step of returning at least a portion of the remaining portion of the aspirate to a grafting site of the body.

23. The method of securing fat cells for micro fat grafting using a syringe of claim 17, further comprising the step of agitating the syringe to promote absorption.

24. The method of securing fat cells for micro fat grafting using a syringe of claim 23, wherein the agitating step includes at least one of the steps of rolling, rotating, and shaking the syringe.

25. The method of securing fat cells for micro fat grafting using a syringe of claim 17, further comprising the step of expelling at least a portion of the remaining portion of the aspirate into one or more syringes.

26. The method of securing fat cells for micro fat grafting using a syringe of claim 17, wherein the retracting step includes retracting the plunger positioned within a second plunger.

27. The method of securing fat cells for micro fat grafting using a syringe of claim 26, wherein the second plunger includes a gasket attached to a proximal end of the second plunger.

* * * * *